US009689825B1

(12) United States Patent
Lim et al.

(10) Patent No.: US 9,689,825 B1
(45) Date of Patent: Jun. 27, 2017

(54) TESTING A LAYER POSITIONED OVER A CAPACITIVE SENSING DEVICE

(71) Applicant: Apple Inc., Cupertino, CA (US)

(72) Inventors: Richard W. Lim, Cupertino, CA (US); Benjamin B. Lyon, Cupertino, CA (US); Srdjan D. Sobajic, Cupertino, CA (US); Giovanni Gozzini, Cupertino, CA (US); Peter G. Panagas, Cupertino, CA (US)

(73) Assignee: Apple Inc., Cupertino, CA (US)

( * ) Notice: Subject to any disclaimer, the term of this patent is extended or adjusted under 35 U.S.C. 154(b) by 252 days.

(21) Appl. No.: 14/481,356

(22) Filed: Sep. 9, 2014

Related U.S. Application Data

(60) Provisional application No. 61/875,618, filed on Sep. 9, 2013.

(51) Int. Cl.
*G01N 27/24* (2006.01)
*G01R 31/28* (2006.01)
*G01R 27/26* (2006.01)

(52) U.S. Cl.
CPC ......... *G01N 27/24* (2013.01); *G01R 27/2605* (2013.01); *G01R 31/2829* (2013.01)

(58) Field of Classification Search
USPC .............. 324/551, 754.03, 658, 755.01, 686, 324/754.21, 149, 663, 690, 71.1, 724, 324/754.07, 754.1, 754.28, 76.11; 345/174, 173; 73/304 C, 514.32, 862.626
See application file for complete search history.

(56) References Cited

U.S. PATENT DOCUMENTS

| 3,434,354 A | | 3/1969 | Voge |
| 3,877,298 A | | 4/1975 | Narang |
| 3,984,767 A | * | 10/1976 | Denton .................. G01B 7/345 |
| | | | 29/593 |
| 4,219,936 A | | 9/1980 | Bridges |

(Continued)

FOREIGN PATENT DOCUMENTS

| CN | 101313224 | 11/2008 |
| CN | 201335849 | 10/2009 |

(Continued)

OTHER PUBLICATIONS

NPL-1: Tianming Chen; Capacitive sensors for measuring complex permittivity of planar and cylindrical structures; Iowa State University; 2012; Graduate Theses and Dissertations. Paper 12294.*

(Continued)

*Primary Examiner* — Melissa Koval
*Assistant Examiner* — Nasima Monsur
(74) *Attorney, Agent, or Firm* — Downey Brand LLP

(57) ABSTRACT

A system for testing a first layer disposed over a capacitive sensing device includes a test probe having a substantially flat conductive test surface, a device under test (DUT) disposed over the capacitive sensing device, and a power supply operatively connected to the test probe. The DUT can include the first layer and one or more additional layers. The substantially flat conductive test surface is positioned over a surface of the DUT and applies power to the DUT. The capacitance between the test probe and at least one capacitive sensing element in the capacitive sensing device is then measured.

20 Claims, 9 Drawing Sheets

(56) References Cited

U.S. PATENT DOCUMENTS

| | | | |
|---|---|---|---|
| 4,245,496 A | 1/1981 | Napetschnig | |
| 4,277,174 A | 7/1981 | Kleesattel | |
| 4,564,408 A | 1/1986 | Crumbach et al. | |
| 4,596,349 A | 6/1986 | Herten | |
| 4,848,141 A | 7/1989 | Oliver et al. | |
| 5,479,827 A | 1/1996 | Kimura et al. | |
| 5,541,525 A | 7/1996 | Wood et al. | |
| 5,616,857 A | 4/1997 | Merck, Jr. et al. | |
| 5,891,744 A | 4/1999 | Lowrey et al. | |
| 5,892,157 A | 4/1999 | Syre | |
| 6,191,593 B1 | 2/2001 | Tartagni et al. | |
| 6,485,913 B1 | 11/2002 | Becker et al. | |
| 6,592,437 B1 | 7/2003 | Boyd et al. | |
| 6,644,160 B1 | 11/2003 | Boselli | |
| 6,884,641 B2 | 4/2005 | Bruley et al. | |
| 6,955,093 B2 | 10/2005 | Smith | |
| 7,032,806 B2 | 4/2006 | Rinne | |
| 7,084,652 B2 | 8/2006 | Guo et al. | |
| 7,267,847 B2 | 9/2007 | Karamuk et al. | |
| 7,521,915 B2 | 4/2009 | Herchen | |
| 7,696,538 B2 | 4/2010 | Lee et al. | |
| 7,733,108 B2 | 6/2010 | Kanev et al. | |
| 7,830,267 B2 | 11/2010 | Veerasamy | |
| 7,968,878 B2 | 6/2011 | Aggarwal et al. | |
| 8,091,437 B2 | 1/2012 | Stumpf | |
| 8,156,794 B2 | 4/2012 | Konaka et al. | |
| 8,253,425 B2 | 8/2012 | Reynolds et al. | |
| 8,821,965 B2 | 9/2014 | Duerig et al. | |
| 8,868,147 B2 | 10/2014 | Stippick et al. | |
| 8,938,993 B2 | 1/2015 | Harper et al. | |
| 8,996,166 B2 | 3/2015 | Jenkinson | |
| 9,086,386 B1 | 7/2015 | Rutherford et al. | |
| 2005/0046428 A1* | 3/2005 | Tesdahl | G01R 31/312 324/658 |
| 2005/0181143 A1 | 8/2005 | Zhang et al. | |
| 2005/0270032 A1* | 12/2005 | McQueeney | F02P 17/12 324/402 |
| 2006/0139041 A1 | 6/2006 | Nystrom et al. | |
| 2007/0144795 A1* | 6/2007 | Tran | G06F 3/044 178/18.06 |
| 2009/0242457 A1 | 10/2009 | Kou | |
| 2010/0230729 A1* | 9/2010 | Ellis-Monaghan | H01L 27/14609 257/228 |
| 2010/0249306 A1 | 9/2010 | Berndt et al. | |
| 2011/0195187 A1 | 8/2011 | Weber et al. | |
| 2012/0275088 A1 | 11/2012 | Huang | |
| 2013/0333485 A1 | 12/2013 | Shah | |
| 2014/0090480 A1 | 4/2014 | Adams et al. | |
| 2014/0360252 A1 | 12/2014 | Yamamoto et al. | |
| 2015/0070037 A1 | 3/2015 | Pragada et al. | |
| 2015/0268273 A1 | 9/2015 | Pragada et al. | |
| 2015/0327370 A1 | 11/2015 | Prest et al. | |

FOREIGN PATENT DOCUMENTS

| | | |
|---|---|---|
| CN | 101617241 | 12/2009 |
| CN | 102081110 | 6/2011 |
| CN | 104359769 | 2/2015 |
| EP | 1834905 | 9/2007 |
| JP | 2011227814 | 11/2011 |
| WO | WO2012/067126 | 5/2012 |

OTHER PUBLICATIONS

NPL-2: Warwick; Capacitive Imaging for NDE; Aug. 28, 2012; https://www2.warwick.ac.uk/fac/sci/eng/research/grouplist/measurement/other/capacitiveimaging/.*

U.S. Appl. No. 14/221,058, filed Mar. 30, 2014, pending.

U.S. Appl. No. 14/271,057, filed May 6, 2014, pending; and.

U.S. Appl. No. 14/450,714, filed Aug. 4, 2014, pending.

Mason et al., "A Generic Multielement Microsystem for Portable Wireless Applications," Proceedings of the IEEE, vol. 86, No. 8, pp. 1733-1746, Aug. 1998.

Schlaak et al., "Micromechanical Capacitive Acceleration Sensor with Force Compensation," Micro Systems Technologies 90, pp. 617-622, 1990.

* cited by examiner

TESTING A LAYER POSITIONED OVER A CAPACITIVE SENSING DEVICE

CROSS-REFERENCE TO RELATED APPLICATION

This application is a nonprovisional patent application of and claims the benefit of U.S. Provisional Patent Application No. 61/875,618, filed Sep. 9, 2013 and titled "Uniformity Testing for a Capacitive Sensing Device," the disclosure of which is hereby incorporated by reference herein in its entirety.

TECHNICAL FIELD

The present invention relates to input devices, and more particularly to a capacitive sensing device. Still more particularly, the present invention relates to a testing a layer positioned over a capacitive sensing device.

BACKGROUND

Capacitive sensing devices are used in a variety of input devices, such as in a trackpad, a touchscreen display, and a fingerprint sensing device. A fingerprint sensing device can capture an image of a fingerprint by measuring the capacitance between the finger and the capacitive sensing elements in the capacitive sensing device. Defects in a layer disposed over the capacitive sensing device can produce errors in the capacitance measurements for one or more capacitive sensing elements. For example, if an air gap is embedded in a layer, the air gap produces a local variation in the dielectric constant of that layer. The fingerprint sensing device may not be able to distinguish the variations produced by a finger touching the fingerprint sensing device from the local variation caused by the air gap. The variation produced by the defect is an additional variation that can result in one or more artifacts in the image of the fingerprint.

SUMMARY

In one aspect, a system for testing a first layer disposed over a capacitive sensing device can include a device under test (DUT), a test probe, and a power supply connected to the test probe. The DUT includes the first layer disposed over the capacitive sensing device. In some embodiments, at least one additional layer can also be disposed over the capacitive sensing device. The test probe can have a substantially flat conductive test surface that is positioned over a top surface of the DUT to energize the DUT (e.g., apply a voltage to the DUT). A removable dielectric layer can be positioned between the capacitive sensing device and the DUT. The removable dielectric layer can fill in and compensate for any unevenness and/or air gaps in the bottom surface of the DUT. The capacitance between the probe and at least one capacitive sensing element in the capacitive sensing device can then be measured. The measured capacitances can be used to determine if the tested first layer has one or more defects that can affect the dielectric constant of the first layer when the fingerprint sensing device captures a fingerprint.

In another aspect, a capacitive sensing device can include a first dielectric layer and a second dielectric layer positioned over the capacitive sensing device. The second layer can be positioned between the first dielectric layer and the capacitive sensing device. A system for testing at least one of the first and second dielectric layers can include a test probe having a substantially flat conductive test surface that is positioned over a top surface of the first dielectric layer. A power supply can be operatively connected to the test probe. A removable dielectric layer can be positioned between the capacitive sensing device and the second dielectric layer. The removable dielectric layer can fill in and compensate for any unevenness and/or air gaps in the bottom surface of the second dielectric layer. The test probe can apply power to the top surface of the first dielectric layer and the capacitance between the probe and at least one capacitive sensing element in the capacitive sensing device is then measured. A processing device can be operatively connected to the testing system to receive the measured capacitances and determine if the test layer includes one or more defects that can affect the dielectric constant of the first layer when the fingerprint sensing device captures a fingerprint.

In another aspect, a capacitive sensing device can include one or more capacitive sensing elements. A first layer can be positioned over the capacitive sensing device. A device under test (DUT) can include at least one layer that is disposed over the capacitive sensing device, where the at least one layer includes the first layer. A method for testing the first layer can include energizing the DUT using a test probe, where the test probe includes a substantially flat conductive test surface that is positioned over a top surface of the DUT. The capacitance of at least one capacitive sensing element can then be measured. A removable dielectric layer can be positioned between the capacitive sensing device and the DUT.

BRIEF DESCRIPTION OF THE DRAWINGS

Embodiments of the invention are better understood with reference to the following drawings. The elements of the drawings are not necessarily to scale relative to each other. Identical reference numerals have been used, where possible, to designate identical features that are common to the figures.

DETAILED DESCRIPTION

Figure 1:
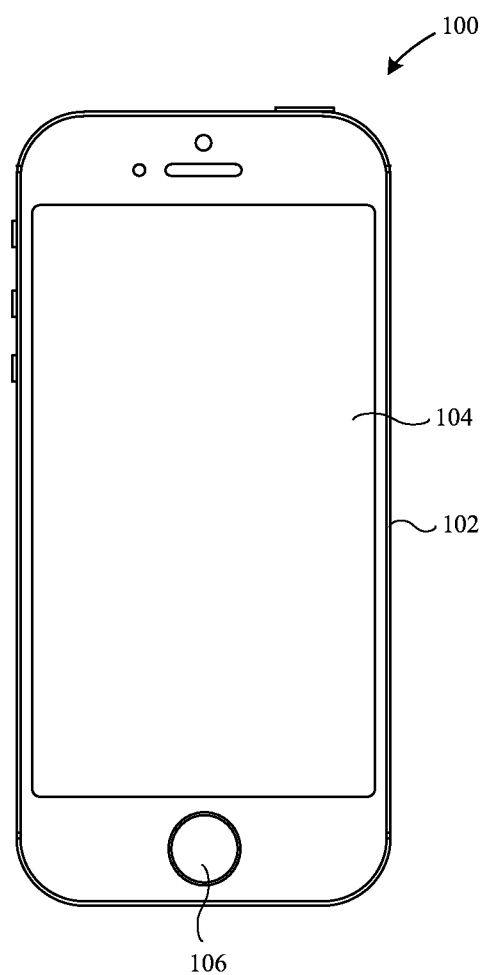
FIG. 1 illustrates an example electronic device that can include a capacitive sensing device.

Embodiments described herein provide a testing system for testing a layer disposed over a capacitive sensing device. The layer to be tested can be a single layer, or the layer to be tested can be included in a stack of two or more layers. The layer to be tested, as well as any additional layers disposed over the capacitive sensing device (e.g., the stack of layers), is referred to herein as a device under test (DUT). The layer is tested to determine if the layer has a suitable uniformity for the capacitive sensing device. Certain defects in the layer can produce a local variation in the dielectric constant of the layer, which can cause the capacitive sensing device to incorrectly measure the capacitance of one or more capacitive sensing elements in the capacitive sensing device.

The testing system can include a test probe having a substantially flat conductive test surface that is positioned over the DUT. A power supply can be operatively connected to the test probe. The substantially flat conductive test surface can energize the DUT, which allows the capacitances of one or more capacitive sensing elements in the capacitive sensing device to be measured. The substantially flat conductive test surface can energize the DUT by applying a voltage to the top surface of the DUT.

In some embodiments, a removable dielectric layer is positioned between the DUT and the capacitive sensing device. The removable dielectric layer can have a dielectric constant that matches or substantially matches the dielectric constant of the layer being tested. The removable dielectric layer can even out the bottom surface of the DUT. For example, the removable dielectric layer can fill in any air gaps or notches in the bottom surface of the DUT. The removable dielectric layer can be formed of any suitable material including, but not limited to, a silicone film, a viscous liquid layer such as oil, and a layer of air.

The testing system can include a processing device that receives the measured capacitances and determines whether the tested layer has a sufficient and/or suitable uniformity. The processing device can store the measured capacitances in a storage device. The processing device can determine if any measured capacitances are outlier values that equal or exceed a threshold value. The processing device can determine a compensation value for each outlier capacitance value that equals or exceeds the threshold value. The one or more compensation values can be determined as part of a calibration procedure, and the one or more compensation values can compensate for respective capacitance values measured by the capacitive sensing device during subsequent sensing operations performed by the capacitive sensing device.

Directional terminology, such as "top", "bottom", "front", "back", "leading", "trailing", etc., is used with reference to the orientation of the Figure(s) being described. Because components of embodiments described herein can be positioned in a number of different orientations, the directional terminology is used for purposes of illustration only and is in no way limiting. When used in conjunction with layers of a display or device, the directional terminology is intended to be construed broadly, and therefore should not be interpreted to preclude the presence of one or more intervening layers or other intervening features or elements. Thus, a given layer that is described as being formed, positioned, disposed on or over another layer, or that is described as being formed, positioned, disposed below or under another layer may be separated from the latter layer by one or more additional layers or elements.

Referring now to FIG. 1, there is shown a perspective view of one example of an electronic device that can include a capacitive sensing device. In the illustrated embodiment, the electronic device 100 is implemented as a smart telephone. Other embodiments can implement the electronic device differently, such as, for example, as a laptop or desktop computer, a tablet computing device, a digital music player, a display input device, a wearable computing device or display, a kiosk, and other types of electronic devices that include a display.

The electronic device 100 includes an enclosure 102 at least partially surrounding a display 104 and one or more buttons 106 or input elements. The enclosure 102 can form an outer surface or partial outer surface and protective case for the internal components of the electronic device 100, and may at least partially surround the display 104. The enclosure 102 can be formed of one or more components operably connected together, such as a front piece and a back piece. Alternatively, the enclosure 102 can be formed of a single piece operably connected to the display 104.

The display 104 can be implemented with any suitable technology, including, but not limited to, a multi-touch sensing touchscreen device that uses liquid crystal display (LCD) technology, light emitting diode (LED) technology, organic light-emitting display (OLED) technology, or organic electroluminescence (OEL) technology. The button 106 can take the form of a home button, which may be a mechanical button, a soft button (e.g., a button that does not physically move but still accepts inputs), an icon or image on a display, and so on. Further, in some embodiments, the button 106 can be integrated as part of a cover glass of the electronic device.

Embodiments of an electronic device can include a capacitive sensing device in the display 104, the home button 106, a portion of the enclosure 102, and/or as a separate electronic device that is connected to another electronic device. By way of example only, the capacitive sensing device can be implemented as a capacitive fingerprint sensing device. The fingerprint sensing device can capture images of one or more fingers in some embodiments. As used herein, the term "image" or "fingerprint image" includes an image and other types of data that can be captured by a capacitive sensing device. By way of example only, a capacitive sensing device can produce a data structure that defines the features in a fingerprint.

A capacitive fingerprint sensing device is described herein to illustrate one embodiment of a capacitive sensing device that includes one or more layers disposed over the capacitive sensing device, where at least one of the layers is tested to determine whether one or more defects are present in the tested layer. Those skilled in the art will recognize that other devices can include one or more layers disposed over a capacitive sensing device. By way of example only, a touchscreen display and a trackpad can include a capacitive sensing device with one or more layers disposed over the capacitive sensing device.

Figure 2:
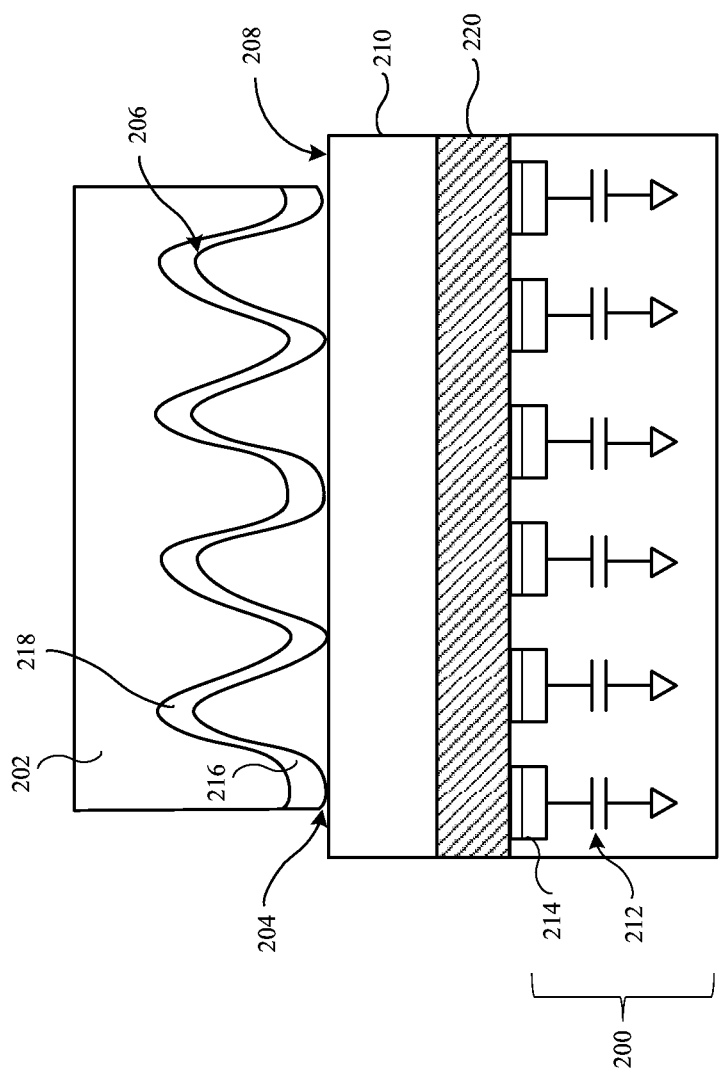
FIG. 2 depicts an enlarged and simplified cross-section view of a portion of a fingerprint sensing device.

FIG. 2 is an enlarged and simplified cross-section view of a finger on a portion of fingerprint sensing device. In the illustrated embodiment, a first layer 210 is included in a stack of layers. By way of example only, the first layer 210 can be a dielectric layer such as a cover glass of display (e.g., display 104 in FIG. 1), an exterior surface of a trackpad, and/or an exterior surface of a button or other input device (e.g., button 106 in FIG. 1). Disposed under the first layer 210 is a second layer 220. By way of example only, the second layer 220 can be a dielectric layer. One example of a dielectric layer is a color layer that reduces the visibility of the capacitive sensing device.

The capacitive fingerprint sensing device 200 can capture an image of a fingerprint of at least a portion of the finger 202 by detecting capacitance changes between the finger and one or more electrodes 214 in the capacitive sensing device. A fingerprint is generally formed from ridges 204 and valleys 206 arranged in a unique pattern. When the finger 202 touches an input region 208 of a first layer 210, the capacitance (represented by capacitors 212) between the finger 202 and one or more electrodes 214 changes, and the variations in the measured capacitance values can be used to capture the fingerprint image.

The skin on the finger 202 includes a dead skin layer 216 disposed over a live skin layer 218. The capacitive sensing device typically images the dead skin layer 216 to obtain an image of the fingerprint. However, if a portion of the dead skin layer 216 is damaged or missing, the capacitive sensing device can obtain an image of the fingerprint by imaging the live skin layer 218 by itself, or by imaging both the remaining dead skin layer 216 and the exposed live skin layer 218.

Figure 3:
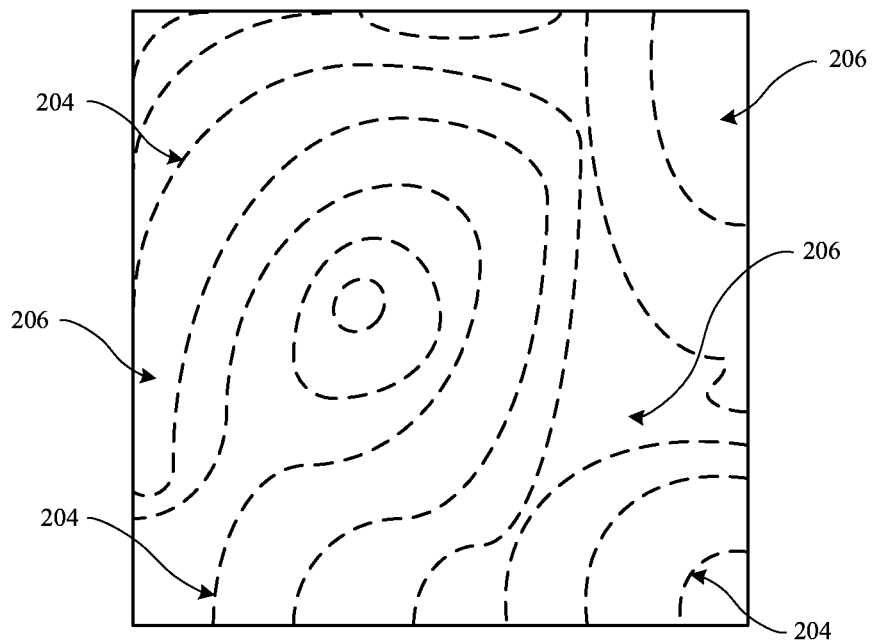
FIG. 3 illustrates a portion of a fingerprint image.

FIG. 3 is a graphic illustration of a portion of a fingerprint image. In FIG. 3, the ridges 204 are represented with dashed lines. The valleys 206 are located in the areas between the ridges 204. Typically, the capacitance measured between a ridge 204 and the capacitive sensing device varies from the capacitance measured between a valley 206 and the capacitive sensing device. The measured capacitance between a ridge and an electrode can be greater than the measured capacitance between a valley and an electrode because the ridge is closer to the electrode. The differences in the measured capacitances can be used to distinguish between ridges and valleys to produce a fingerprint image.

Figure 4:
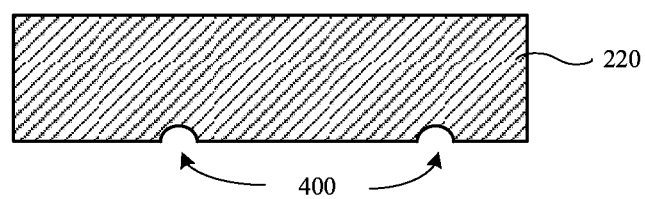
FIG. 4 depicts an example defect that can be present in a layer positioned over a capacitive sensing device.

Referring now to FIG. 4, there is shown an example defect that can be present in a layer positioned over a capacitive sensing device. For example, the layer can be the first layer 210 or the color layer 220. The defect 400 is located in the color layer 220 in the illustrated embodiment. The defect is formed in one or more surfaces of the layer, and is referred to herein as a topological defect 400. Topological defects can have any size and can be as small as ten microns. In some embodiments, topological defects 400 may be detected or viewed with a microscope, an on-machine measurement (OMM) system, or other types of inspection devices.

Figure 5:
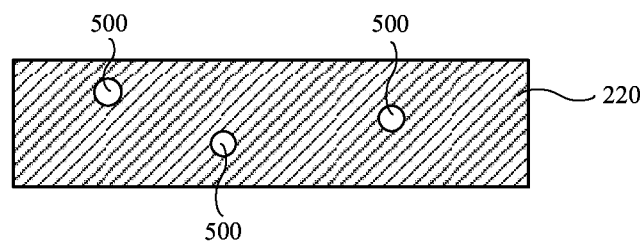
FIG. 5 illustrates another example defect that can be present in a layer positioned over a capacitive sensing device.

Other types of defects may not be detectable by various inspection systems. FIG. 5 illustrates another example defect that can be present in a layer positioned over a capacitive sensing device. Again, the defect is located in the color layer 220 in the illustrated embodiment. The defect is embedded in the layer 220, and is referred to herein as an embedded defect 500. The embedded defect can be a void (i.e., air gap) or a metallic or non-metallic particle in the layer. Voids and non-metallic particles may not be detected with computed tomography (CT) scan or an x-ray image. Additionally, a void or a metallic or non-metallic particle that is small in size, as small as 10 microns, may not be detected by inspection devices, including a confocal scanning acoustic microscope (CSAM).

The capacitance of a capacitor is a function of the area of the electrodes and the dielectric constant of the material between the electrodes. With the fingerprint sensing device shown in FIG. 2, one electrode is the user's finger, the other electrode is an electrode 214, and the material between the electrodes is the first layer 210 and the color layer 220. A finger imposed on the first layer 210 can cause variations in the dielectric constant of the layers. A defect in the first layer 210 or in the color layer 220 can also produce a local variation in the dielectric constant of the layer that includes the defect. The fingerprint sensing device may not be able to distinguish the variations caused by the finger from the variation caused by the defect. The variation produced by the defect is an additional variation that can result in one or more artifacts in the image of the fingerprint. Embodiments described herein can be used to determine whether one or more layers positioned over a capacitive sensing device has a defect or defects. The testing device can determine if one or more embedded and/or topological defects are present in a layer.

Figure 6:
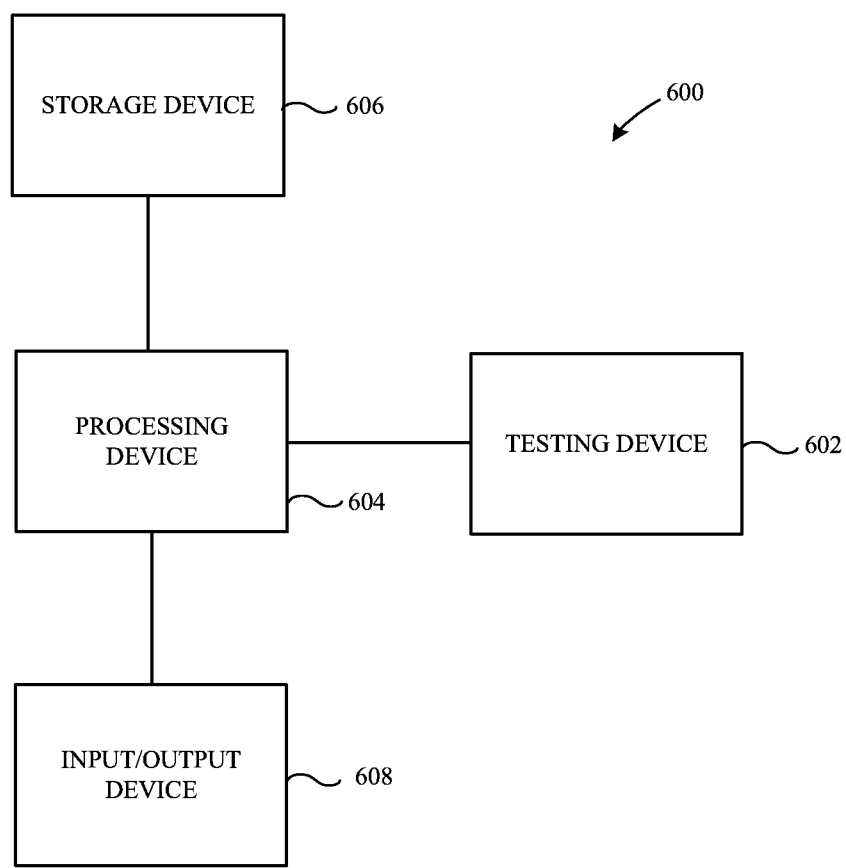
FIG. 6 is a block diagram of a testing system for testing at least one layer that is to be positioned over a capacitive sensing device.

Referring now to FIG. 6, there is shown a block diagram of a testing system for testing at least one layer that is to be positioned over a capacitive sensing device. The testing system 600 can include a testing device 602 operatively connected to one or more processing devices 604, one or more storage devices 606, and one or more input/output (I/O) device(s) 608. The processing device(s) 604 can communicate, either directly or indirectly, with substantially all of the components of the testing system 600. The processing device or devices can control some or all of the operations of the testing device 602, receive and process test data from the testing device, and store the test data or operational and control data for the testing device 602 in the storage device 606. The processing device(s) 604 can be implemented as any electronic device capable of processing, receiving, or transmitting data or instructions. For example, the one or more processing devices 604 can be a microprocessor, a central processing unit (CPU), an application-specific integrated circuit (ASIC), a digital signal processor (DSP), or combinations of multiple such devices. As described herein, the term "processing device" is meant to encompass a single processor or processing unit, multiple processors, multiple processing units, or other suitably configured computing element or elements.

The storage device(s) 606 can store electronic data that can be used by the testing system 600. For example, a storage device can store electrical data or content such as, for example, test signals and timing signals for the testing device. The storage device(s) 606 can store test data produced when testing one or more layers positioned over a capacitive sensing device. Additionally or alternatively, the storage device 606 can store compensation values that are determined for the capacitive sensing device during or after the layer or layers have been tested. The storage device(s) 606 can be configured as any type of memory. By way of example only, the memory can be implemented as random access memory, read-only memory, Flash memory, removable memory, or other types of storage elements, in any combination. The memory can be included in the testing system, in an electronic device that includes the capacitive sensing device, and/or in another electronic device operatively connected to the electronic device that includes the capacitive sensing device. For example, the storage device can be a server that is connected to the testing system and/or to the electronic device that includes the capacitive sensing device through any wired or wireless connection.

The input/output device(s) 608 can receive data from a user or one or more other electronic devices. Additionally, the input/output device(s) 608 can facilitate transmission of data to a user or to other electronic devices. For example, the I/O device 608 can transmit electronic signals via a wireless or wired connection. Examples of wireless and wired connections include, but are not limited to, WiFi, Bluetooth, IR, and Ethernet. Additionally, the I/O device(s) 608 can include a display that displays information relating to the testing device 602 the tests performed by the testing device, and/or the test results produced by the testing device 602.

Figure 7:
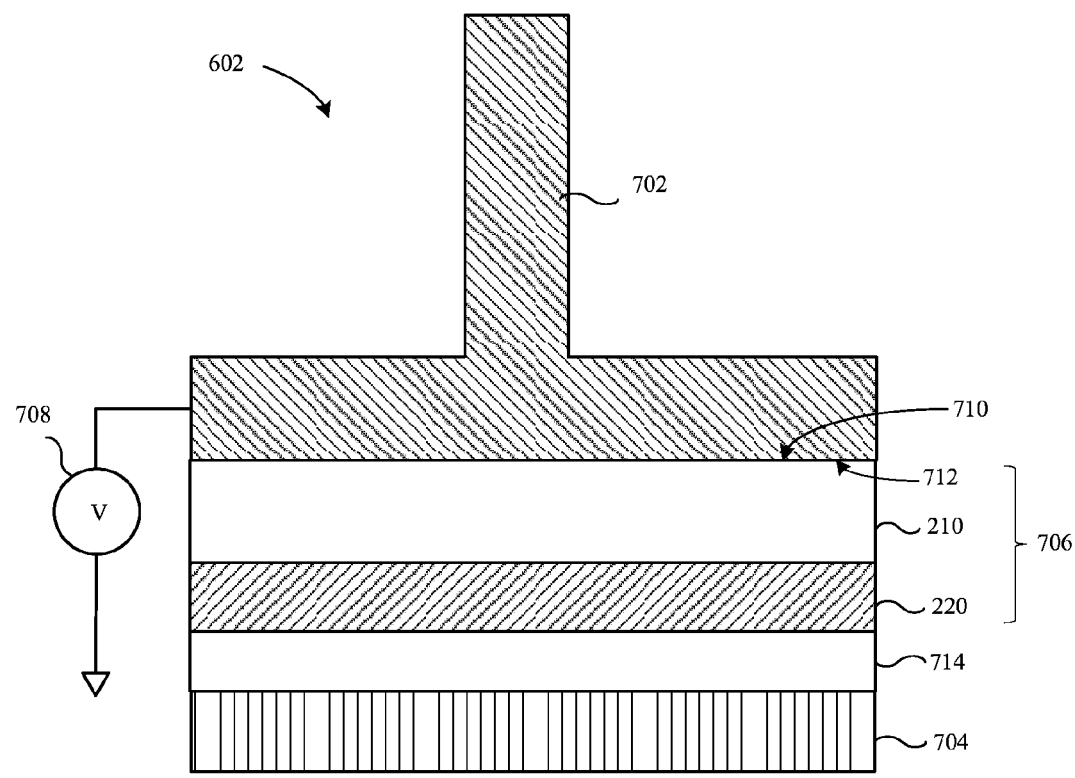
FIG. 7 depicts a portion of the testing device 602 testing a layer positioned over a capacitive sensing device.

FIG. 7 depicts a portion of a testing device testing a layer positioned over a capacitive sensing device. The testing device 602 includes a test probe 702, the first layer 210 (FIG. 2), the color layer 220, and a capacitive sensing device 704. In some embodiments, the capacitive sensing device is included in an integrated circuit. The capacitive sensing device 704 can include one or more electrodes and/or one or more layers of one or more electrodes. For example, a single layer of multiple electrodes 214 is shown in FIG. 2.

In the illustrated embodiment, the color layer 220 is tested for defects using the probe 702. The layer or layers positioned over the capacitive sensing device 704 are referred to herein as the device under test (DUT) 706. Thus, the DUT 706 includes the layer to be tested and optionally one or more additional layers that are positioned over the capacitive sensing device. For example, the first layer 210 in FIG. 7 is an additional layer included in the DUT 706 and the color layer 220 is the layer to be tested. In some embodiments, the one or more additional layers in the DUT can be tested separately from the layer to be tested, tested simultaneously with the layer to be tested, or not tested at all.

During testing, the capacitance between the test probe 702 and the capacitive sensing device 704 is measured. A power supply 708 is operatively connected to the probe 602 and to a reference voltage, such as ground. The power supply can be an alternating current (AC) or direct current (DC) power supply. The test probe 702 can have a substantially flat conductive test surface 710 that is disposed over, or in contact with the top surface of the DUT 706 to apply power (e.g., a voltage) to the DUT. In the illustrated embodiment, the conductive test surface 710 is put in contact with the top surface 712 of the first layer 210. Generally, the top surface 712 of the first layer 210 is substantially flat so that the conductive test surface 710 can be substantially flush with the top surface 712 of the first layer 210.

The bottom surface of the color layer 220 may or may not be planar or flat. For example, an air gap or a notch (i.e., a topological defect) may be formed in the bottom surface of the color layer 220. Thus, in some embodiments, a removable dielectric layer 714 is disposed between the DUT 706 and the capacitive sensing device 704 to fill in and flatten the bottom surface of the color layer 220. In one embodiment, a dielectric constant of the removable dielectric layer 714 matches or substantially matches the dielectric constant of the layer being tested. Thus, in the illustrated embodiment, the dielectric constant of the removable dielectric layer 714 substantially matches the dielectric constant of the color layer 220. The removable dielectric layer can be comprised of any suitable material including, but not limited to, a silicone film, a viscous liquid layer such as oil, and a layer of air.

The capacitance between the test probe and one or more electrodes in the capacitive sensing device 704 can be measured while the test probe 702 energizes (e.g., applies a voltage to) the top surface of the first layer 210. In one embodiment, the capacitance of a single capacitive sensing element is measured. As used herein, the term "capacitive sensing element" refers to the capacitance between the test probe and one electrode or one electrode pair in the capacitive sensing device. An electrode pair can be formed in a capacitive sensing device by two electrodes positioned in a spaced apart relationship, or one electrode spaced apart from a conductive layer. The capacitances of one or more individual capacitive sensing elements can be measured sequentially. The measured capacitances can be received by a processing device (e.g., processing device 602) to determine if one or more embedded defects and/or one or more topological defects are present in the color layer 220.

Figure 8A:
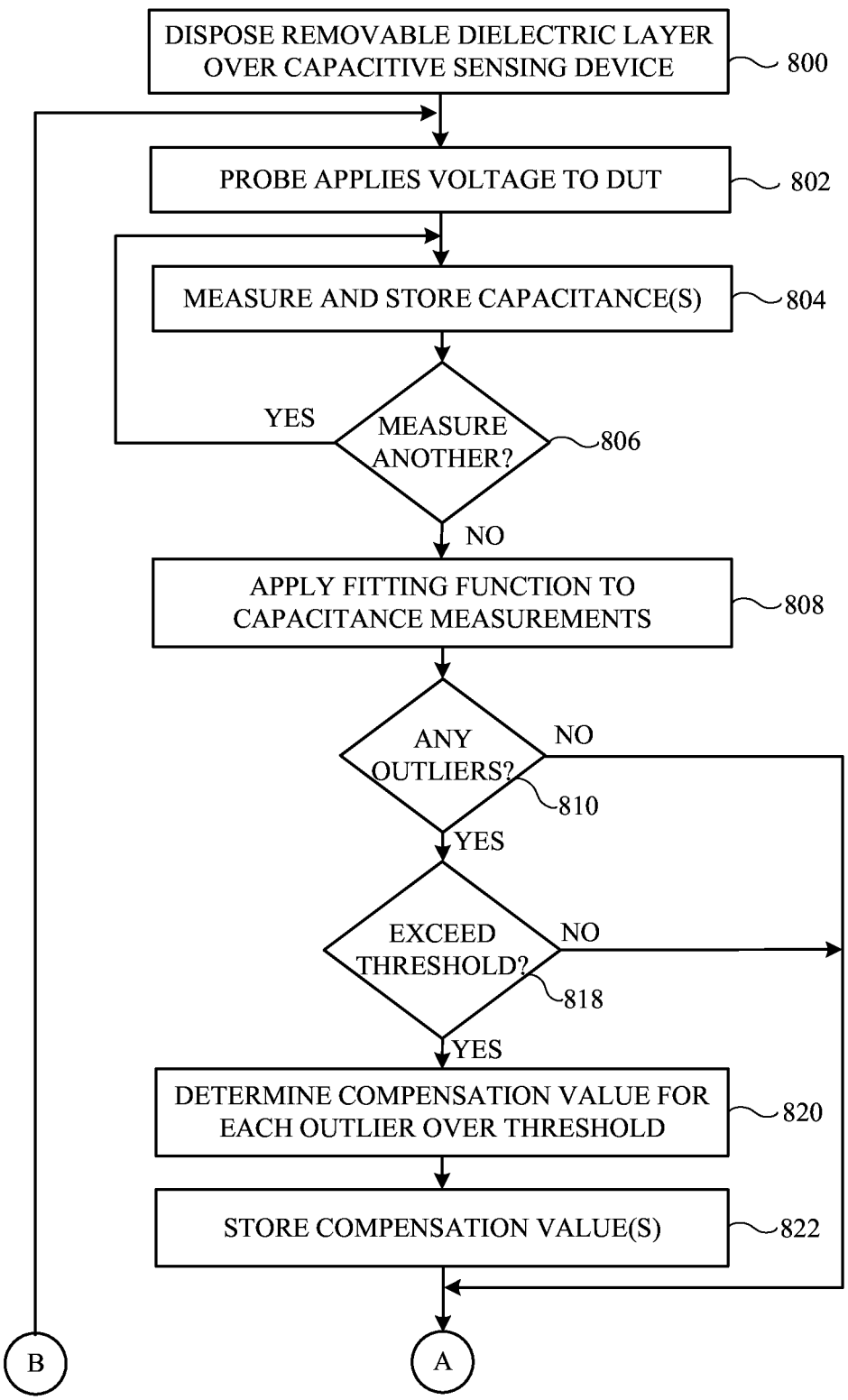
FIGS. 8A-8B illustrate a flowchart of one example method for testing for defects in a layer positioned over a capacitive sensing device.
Figure 8B:
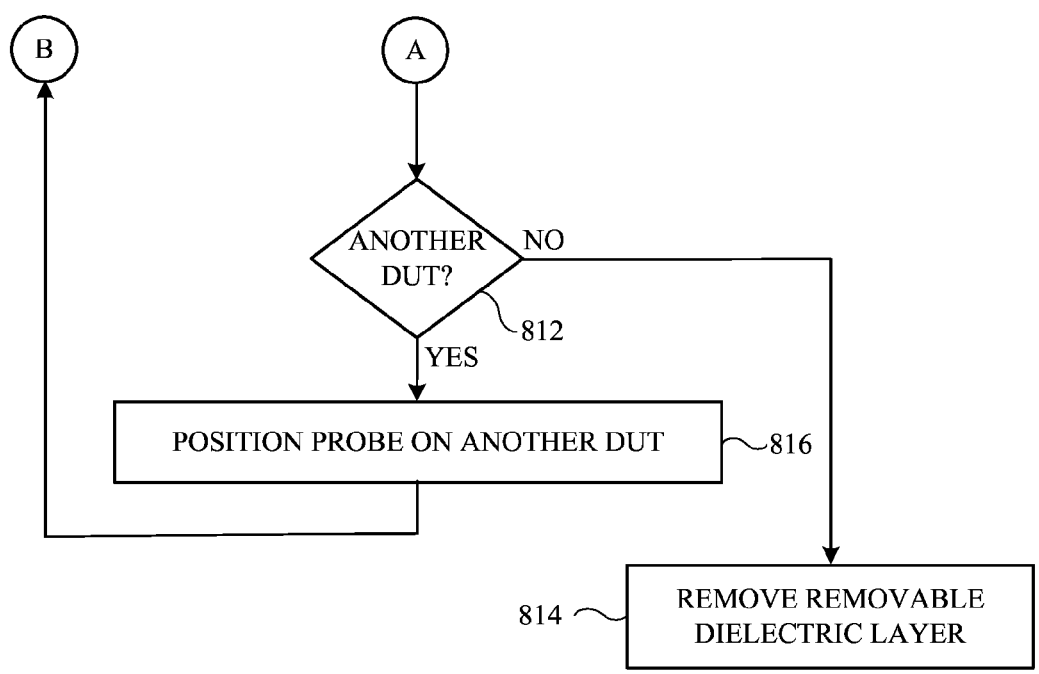

Referring now to FIGS. 8A-8B, there is shown a flowchart of a method for testing for defects in a layer positioned over a capacitive sensing device. Initially, a removable dielectric layer is disposed over a top surface of the capacitive sensing device (block 800). The removable dielectric layer can be selected such that a dielectric constant of the removable dielectric layer substantially matches a dielectric constant of the layer to be tested. For example, in the embodiment shown in FIG. 7, the dielectric constant of the removable dielectric layer 714 may substantially match the dielectric constant of the color layer 220.

Next, as shown in block 802, a test probe is positioned over a DUT and energizes the DUT. By way of example only, the substantially flat conductive test surface of the test probe can apply a voltage to the top surface of the DUT. The capacitance of one or more capacitive sensing elements is then measured at block 804. As described earlier, the capacitance of a single capacitive sensing element is measured at a time in one embodiment. Other embodiments can measure the capacitances of two or more capacitive sensing elements at a time. The measured capacitance or capacitances can be stored in a storage device, such as storage device 606 in FIG. 6.

A determination is then made at block 806 as to whether or not the capacitance of another capacitive sensing element is to be measured. If so, the process returns to block 804 and repeats until the capacitances of all of the capacitive sensing elements have been measured. When the capacitance of another capacitive sensing element will not be measured at block 806, the method passes to block 808 where a fitting function is applied to the measured capacitances. Any suitable fitting function can be used at block 808. By way of example only, the fitting function can be a Gaussian function or a curve fitting function.

Figure 9:
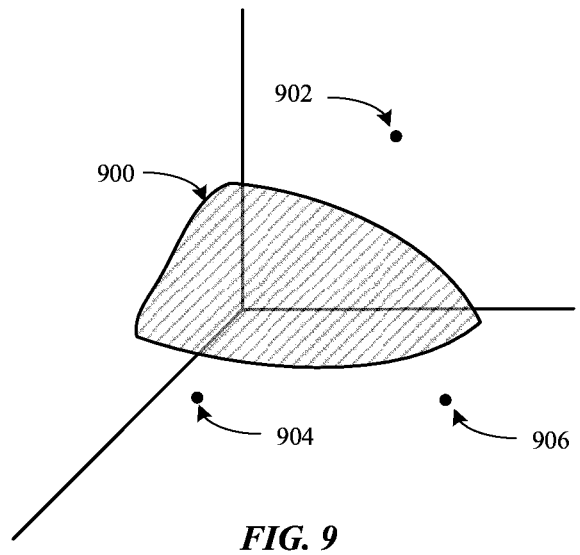
FIG. 9 depicts blocks 808 and 810 of FIG. 8.

A determination is then made at block 810 as to whether one or more outlier capacitances are present in the capacitance measurements. FIG. 9 illustrates blocks 808 and 810 of FIG. 8. In the illustrated embodiment, a fitting function is applied to the capacitance measurements to produce a three-dimensional surface 900. Three outlier capacitances 902, 904, 906 are also produced by the fitting function. In other embodiments, a fitting function can represent the capacitance measurements differently. For example, a histogram or a conic section can be used to map the fitted capacitance measurements.

If there are no outlier capacitances at block 810, the process passes to block 812 where a determination is made as to whether or not another DUT is to be tested. If another DUT will not be tested, the method continues at block 814 where the removable dielectric layer can be removed from the surface of the capacitive sensing device and the method ends. Block 814 can be optional, and in some embodiments the dielectric layer may not need to be removed, such as when the dielectric layer is air, or the dielectric layer may remain between the DUT and the capacitive sensing device.

If another DUT is to be tested at bock 812, the process passes to block 816 where the probe is positioned over the next DUT to be tested. The probe can be positioned by moving the probe over the next DUT, by moving the DUT such that the probe is positioned over the DUT, or by moving both the DUT and the probe. The process returns to block 802 once the probe is positioned over the next DUT.

Returning to block 810, if there are one or more outlier capacitances, a determination is made at block 818 as to whether or not the outlier capacitance(s) equal or exceed a threshold value. Any suitable threshold value can be used in block 818. For example, in one embodiment, a threshold value can be a given percentage of the fitted surface capacitance measurement. Alternatively, in another embodiment, a threshold value can be a fixed difference or value.

If the outlier capacitance(s) do not equal or exceed the threshold value, the method passes to block 812. If one or more outlier capacitances equal or exceed the threshold value, the process continues at block 820 where a compensation value is determined for each outlier capacitance. By way of example only, a compensation value can be the difference between the actual measured capacitance and an expected fitted capacitance value. Thus, a compensation value for outlier capacitance 904 in FIG. 9 can be the difference between the actual measured capacitance 904 and an expected point on the surface 900.

Next, as shown in block 822, the compensation value or values can be stored in a storage device. An example storage device 604 is depicted in FIG. 6. The method then continues at block 812. If another DUT will be tested, the process returns to block 802 and repeats until all of the DUTs have been tested. The method ends after all of the DUTs are tested.

Other embodiments can perform the method shown in FIG. 8 differently. For example, blocks can be omitted, blocks can be added, or the blocks can be performed in a different order. As one example, block 818 can be omitted in some embodiments.

Figure 10:
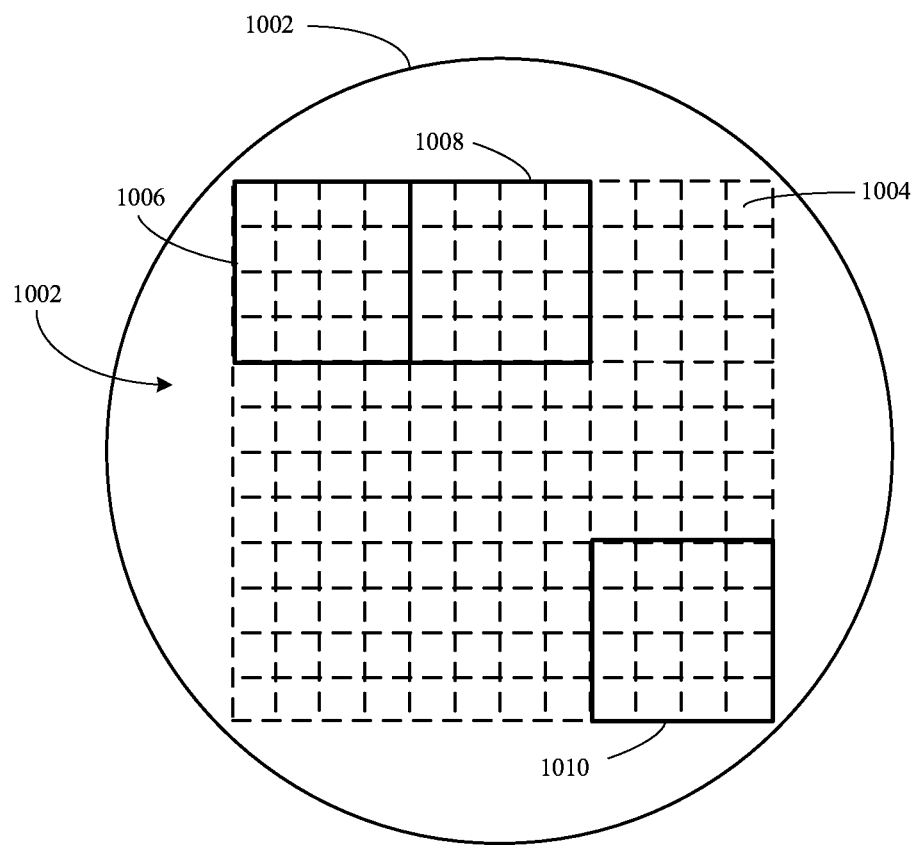
FIG. 10 illustrates blocks 810 and 812 of FIG. 8.

FIG. 10 is used to illustrate blocks 812 and 816 of FIG. 8. A capacitive sensing device 1000 can be included in an integrated circuit 1002. The integrated circuit can have any given dimension and/or shape. Additionally, components other than the capacitive sensing device 1000 can be included in the integrated circuit. For example, a processing channel that receives signals from the capacitive sensing device can be included in the integrated circuit. The processing channel can include an amplifier connected to an analog-to-digital converter (ADC). Additional amplifiers can be connected in series to the amplifier connected to the ADC.

The test probe can test a portion of the capacitive sensing elements 1004 at a time in the illustrated embodiment. Thus, the test probe can test a first group of capacitive sensing elements 1006. In some embodiments, each capacitive sensing element in a group is tested one at a time. Once all of the capacitive sensing elements 1004 in the first group are tested, the test probe can be positioned over a second group of capacitive sensing elements 1008. The process of testing and repositioning the test probe can repeat until the last group of capacitive sensing elements 1010 has been tested.

Figure 11:
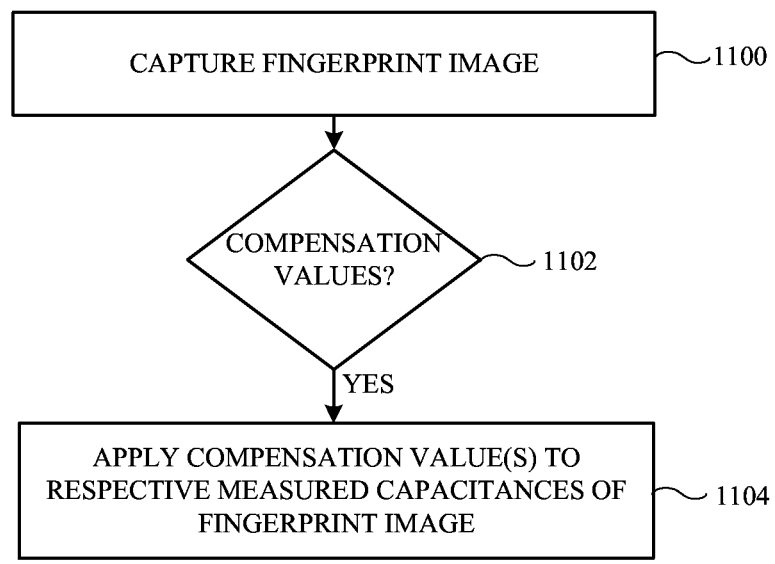
FIG. 11 depicts a flowchart of one example method for operating a capacitive sensing device.

Referring now to FIG. 11, there is shown a flowchart of a method for operating a capacitive fingerprint sensing device. The method is performed after performing the method shown in FIG. 8. Initially, the capacitive fingerprint sensing device captures a fingerprint image at block 1100. A determination is then made at block 1102 as to whether any compensation values have been determined for this capacitive fingerprint sensing device. If not, the method ends. If one or more compensation values have been determined for the fingerprint sensing device, the process continues at block 1104 where each compensation value is applied to a respective measured capacitance of the fingerprint image. The one or more compensation values can be read out of a storage device (e.g., storage device 606 in FIG. 6). The method ends after the compensation value or values are applied to the fingerprint image. In some embodiments, additional processing steps can be performed on the fingerprint image, such as, for example, noise compensation, deblurring, and encryption.

Various embodiments have been described in detail with particular reference to certain features thereof, but it will be understood that variations and modifications can be effected within the spirit and scope of the disclosure. For example, a device other than a touch sensing device and/or a force sensing device can share at least a portion of the display area. By way of example only, a fingerprint sensing device can use at least a portion of the top surface of the display as an input region.

Even though specific embodiments have been described herein, it should be noted that the application is not limited to these embodiments. In particular, any features described with respect to one embodiment may also be used in other embodiments, where compatible. Likewise, the features of the different embodiments may be exchanged, where compatible.

We claim:

1. A system for testing a dielectric layer disposed over a capacitive sensing device, the capacitive sensing device having multiple electrodes, the system comprising:
   a test probe disposed over the dielectric layer such that the dielectric layer forms a dielectric body positioned between the test probe and the capacitive sensing device; and
   a power supply that supplies a voltage to the test probe, wherein the voltage energizes multiple capacitive regions within the dielectric body formed by the test probe and the multiple electrodes, wherein each of the multiple capacitive regions, when energized, has a measurable capacitance value used to determine a compensation value; and
   a storage device, wherein when the measurable capacitance value exceeds a threshold capacitance value defining an outlier capacitance value, the storage device applies the compensation value to the outlier capacitance value, the compensation value altering the outlier capacitance value to be within the threshold capacitive value.

2. The system as in claim 1, wherein the multiple capacitive regions include a capacitor, and when the measurable capacitance value of the capacitor exceeds a threshold capacitance value, the storage device applies the compensation value to the capacitor.

3. The system as in claim 1, further comprising a second dielectric layer positioned between the dielectric layer and the test probe, the second dielectric layer further defining the dielectric body, wherein the second dielectric layer includes one of a cover glass, a track pad, or a button of an electronic device.

4. The system as in claim 1, further comprising a removable dielectric layer positioned between the dielectric layer and the capacitive sensing device, wherein a dielectric constant of the removable dielectric layer substantially matches a dielectric constant of the layer.

5. The system as in claim 1, wherein the dielectric layer comprises a color layer.

6. The system as in claim 1, wherein the capacitive sensing device comprises a capacitive fingerprint sensing device.

7. A method for testing a layer positioned over a capacitive sensing device that includes multiple capacitive sensing elements, the method comprising:
   energizing the layer with a test probe, wherein the layer is positioned between the test probe and the capacitive sensing device;
   measuring a capacitance value of each of the multiple capacitive sensing elements to define measured capacitances;
   applying a fitting function to the measured capacitances to define fitted measured capacitances;

determining whether an outlier capacitance value is present in the fitted measured capacitances, the outlier capacitance value exceeding a threshold capacitance value; and when the outlier capacitance value is present, applying from a storage device a compensation value to the outlier capacitance value that alters the outlier capacitance value to be within the threshold capacitive value.

8. The method as in claim 7, wherein energizing the layer with the test probe comprises applying with the test probe a voltage to the layer.

9. The method as in claim 7, further comprising a second layer positioned between the layer and the test probe, the layer and the second layer defining a dielectric body.

10. The method as in claim 9, further comprising positioning a removable dielectric layer between the layer and the capacitive sensing device.

11. The method as in claim 7, wherein measuring the capacitance value of each of the multiple capacitive sensing elements comprises measuring a capacitance of each of the multiple capacitive sensing elements one at a time until all of the multiple capacitive sensing elements in the capacitive sensing device have been tested.

12. The method as in claim 7, further comprising:
   determining if another layer is to be tested; and
   when another layer is to be tested, positioning the test probe over the other layer.

13. A system for testing a layer disposed over a capacitive sensing device, the system comprising:
   a test probe;
   a first dielectric layer;
   a second dielectric layer, wherein the first dielectric layer and the second dielectric layer are positioned between the test probe and the capacitive sensing device;
   a storage device that stores a compensation value; and
   a power supply that supplies electrical current to the test probe such that the test probe and the capacitive sensing device form a capacitor having a measured capacitance based upon the first dielectric layer and the second dielectric layer, wherein when at least one of the first dielectric layer and the second dielectric layer includes a defect, the measured capacitance corresponds to an outlier capacitance, and the storage device applies the compensation value to the outlier capacitance.

14. The system as in claim 13, further comprising a third dielectric layer removably positioned between the second dielectric layer and the capacitive sensing device.

15. The system as in claim 14, wherein a dielectric constant of the third dielectric layer substantially matches a dielectric constant of the first layer.

16. The system as in claim 14, wherein a dielectric constant of the third dielectric layer substantially matches a dielectric constant of the second layer.

17. The system as in claim 13, wherein the second dielectric layer comprises a color layer.

18. The system as in claim 13, further comprising a processing device operatively connected to the test probe.

19. The system as in claim 13, wherein a fitting function is applied to the measured capacitance to determine whether the measured capacitance corresponds to the outlier capacitance.

20. The system as in claim 13, wherein the capacitive sensing device comprises multiple electrodes such that multiple capacitors are formed from the test probe and the multiple electrodes, and wherein each of the multiple capacitors is measured to determine 1) a presence of outlier capacitances, and 2) whether the storage device applies the compensation value to the outlier capacitances.

* * * * *